US011832787B2

(12) United States Patent
Freedman et al.

(10) Patent No.: US 11,832,787 B2
(45) Date of Patent: Dec. 5, 2023

(54) USER-INTERFACE WITH NAVIGATIONAL AIDS FOR ENDOSCOPY PROCEDURES

(71) Applicant: Verily Life Sciences LLC, South San Francisco, CA (US)

(72) Inventors: Daniel Freedman, Haifa (IL); Yacob Yochai Blau, Haifa (IL); Dmitri Veikherman, Ness Ziona (IL); Roman Goldenberg, Haifa (IL); Ehud Rivlin, Haifa (IL)

(73) Assignee: Verily Life Sciences LLC, South San Francisco, CA (US)

( * ) Notice: Subject to any disclaimer, the term of this patent is extended or adjusted under 35 U.S.C. 154(b) by 0 days.

(21) Appl. No.: 17/562,599

(22) Filed: Dec. 27, 2021

(65) Prior Publication Data

US 2022/0369895 A1 Nov. 24, 2022

Related U.S. Application Data

(60) Provisional application No. 63/192,479, filed on May 24, 2021.

(51) Int. Cl.
*A61B 1/00* (2006.01)
*G06T 11/20* (2006.01)
(Continued)

(52) U.S. Cl.
CPC .......... *A61B 1/0005* (2013.01); *G06T 11/001* (2013.01); *G06T 11/206* (2013.01); *A61B 1/31* (2013.01); *G06T 2200/24* (2013.01)

(58) Field of Classification Search
CPC .................................................. A61B 1/0005
(Continued)

(56) References Cited

U.S. PATENT DOCUMENTS 7,889,227 B2 * 2/2011 Rahn ................... G06F 3/04845
  348/45
2007/0061726 A1 * 3/2007 Rahn ..................... G06T 19/003
  345/629
(Continued)

FOREIGN PATENT DOCUMENTS

| WO | 2020242949 A1 | 12/2020 |
| WO | 2020245815 A1 | 12/2020 |
| WO | 2021011190 A1 | 1/2021 |

OTHER PUBLICATIONS

International Search Report and Written Opinion, dated Sep. 23, 2022, in corresponding International Patent Application No. PCT/US2022/029872, 12 pages.
(Continued)

*Primary Examiner* — Reza Nabi
(74) *Attorney, Agent, or Firm* — Christensen O'Connor Johnson Kindness PLLC

(57) ABSTRACT

A user-interface for aiding navigation of an endoscope through a lumen of a tubular anatomical structure during an endoscopy procedure includes a video region in which a live video feed received from the endoscope is displayed and an observation location map. The observation location map depicts a point of observation from which the live video feed is acquired within the lumen relative to a cross-sectional depiction of the lumen as the endoscope longitudinally traverses the tubular anatomical structure within the lumen during the endoscopy procedure.

24 Claims, 10 Drawing Sheets

(51) Int. Cl.
  *G06T 11/00* (2006.01)
  *A61B 1/31* (2006.01)
(58) Field of Classification Search
  USPC .......................................................... 715/719
  See application file for complete search history.

(56) References Cited

U.S. PATENT DOCUMENTS

| | | | |
|---|---|---|---|
| 2008/0161642 A1 | 7/2008 | Hale et al. | |
| 2008/0207997 A1* | 8/2008 | Higgins | A61B 90/36 600/114 |
| 2009/0063118 A1* | 3/2009 | Dachille | G06T 7/0012 703/11 |
| 2009/0177094 A1* | 7/2009 | Brown | A61B 5/0066 606/2 |
| 2010/0215226 A1* | 8/2010 | Kaufman | G06T 3/0037 382/128 |
| 2016/0078625 A1* | 3/2016 | Tajbakhsh | G06T 7/0012 382/128 |
| 2016/0217573 A1* | 7/2016 | Lian | G06T 5/20 |
| 2017/0046835 A1* | 2/2017 | Tajbakhsh | G06T 7/13 |
| 2017/0186154 A1* | 6/2017 | Chi | A61B 1/000095 |
| 2018/0225820 A1* | 8/2018 | Liang | G16H 20/40 |
| 2018/0253839 A1* | 9/2018 | Zur | G06T 7/0012 |
| 2018/0263568 A1* | 9/2018 | Yi | A61B 1/000094 |
| 2019/0297276 A1* | 9/2019 | Sachdev | G06T 7/0012 |
| 2020/0178948 A1* | 6/2020 | Piskun | A61B 1/018 |
| 2020/0281454 A1* | 9/2020 | Refai | A61B 90/39 |
| 2020/0387706 A1* | 12/2020 | Zur | G06T 7/0012 |
| 2021/0280312 A1* | 9/2021 | Freedman | G06V 10/764 |
| 2022/0254017 A1* | 8/2022 | Rivlin | A61B 5/7267 |
| 2022/0369895 A1* | 11/2022 | Freedman | A61B 1/0005 |
| 2022/0369899 A1* | 11/2022 | Lack | A61B 1/31 |
| 2022/0369920 A1* | 11/2022 | Freedman | G06T 7/0012 |
| 2022/0378400 A1* | 12/2022 | Yu | A61B 8/5215 |

OTHER PUBLICATIONS

Freedman, et al., Detecting Deficient Coverage in Colonoscopies, IEEE Transactions on Medical Imaging, Jan. 23, 2020, 10 pages.
Freedman et al., Detecting Deficient Coverage in Colonoscopies, arxiv.org, Cornell University Library, Jan. 23, 2020, 12 pages.
Ma et al., Real-Time 3D Reconstruction of Colonoscopic Surfaces for Determining Missing Regions, Advances in Intelligent Data Analysis, XIX, Oct. 10, 2019, 10 pages.
Endo-Aid CADe: real-time computer aided detection for endoscopy, Olympus, http://www.olympus.eu/evisx1, Oct. 9, 2020, 4 pages.
Freedman et al., Using Machine Learning to Detect Deficient Coverage in Colonscopy Screenings, https:///ai.googleblog.com/2020/08/usiing-machine-learning-to-detect.html; Aug. 28, 2020, 4 pages.
Freedman et al., Detecting Deficient Coverage in Colonoscopies, IEEE Transactions on Medical Imaging, vol. 39, No. 11, Nov. 2020, 12 pages.
Scopepilot—The Next Generation 3D colon navigation system, Pentax Medical, May 24, 2021, date downloaded from web https://www.pentaxmedical.com/pentax/en/95/2/SCOPEPILOT-The-next-generation-3D-colon-navigation-system, 7 pages.
GI Genius intelligent endoscopy module, medtronic.com/gi, 2021, 11 pages.

\* cited by examiner

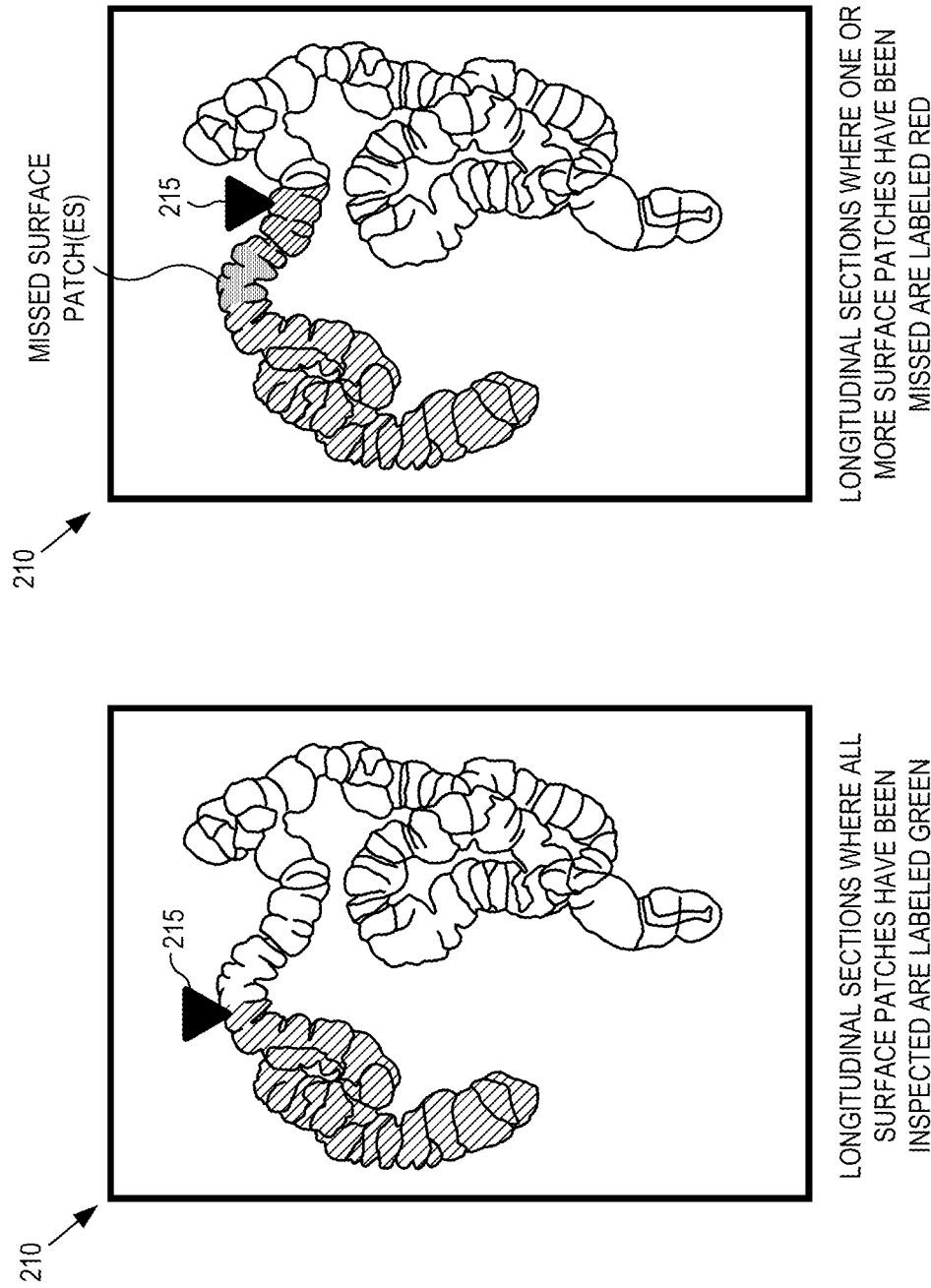

USER-INTERFACE WITH NAVIGATIONAL AIDS FOR ENDOSCOPY PROCEDURES

CROSS-REFERENCE TO RELATED APPLICATIONS

This application claims the benefit of U.S. Application No. 63/192,479, filed on May 24, 2021, the contents of which are incorporated herein by reference.

TECHNICAL FIELD

This disclosure relates generally to endoscopy, and in particular, but not exclusively, to user-interfaces to aid colonoscopy.

BACKGROUND INFORMATION

When an endoscopist performs a colonoscopy, one of the most important tasks during the withdrawal phase is to ensure that they have visualized every surface of the colon in order to detect all the polyps. 20% to 24% of polyps that have the potential to become cancerous (adenomas) are missed. Two major factors that may cause an endoscopist to miss a polyp are: (1) the polyp appears in the field of view, but the endoscopist misses it, perhaps due to its small size or flat shape; and (2) the polyp does not appear in the field of view, as the endoscopist has not fully covered the relevant area during the procedure.

Conventional products that assist clinicians/endoscopists with detecting polyps do not currently support features for coverage visualization.

BRIEF DESCRIPTION OF THE DRAWINGS

Non-limiting and non-exhaustive embodiments of the invention are described with reference to the following figures, wherein like reference numerals refer to like parts throughout the various views unless otherwise specified. Not all instances of an element are necessarily labeled so as not to clutter the drawings where appropriate. The drawings are not necessarily to scale, emphasis instead being placed upon illustrating the principles being described.

DETAILED DESCRIPTION

Figure 1A:
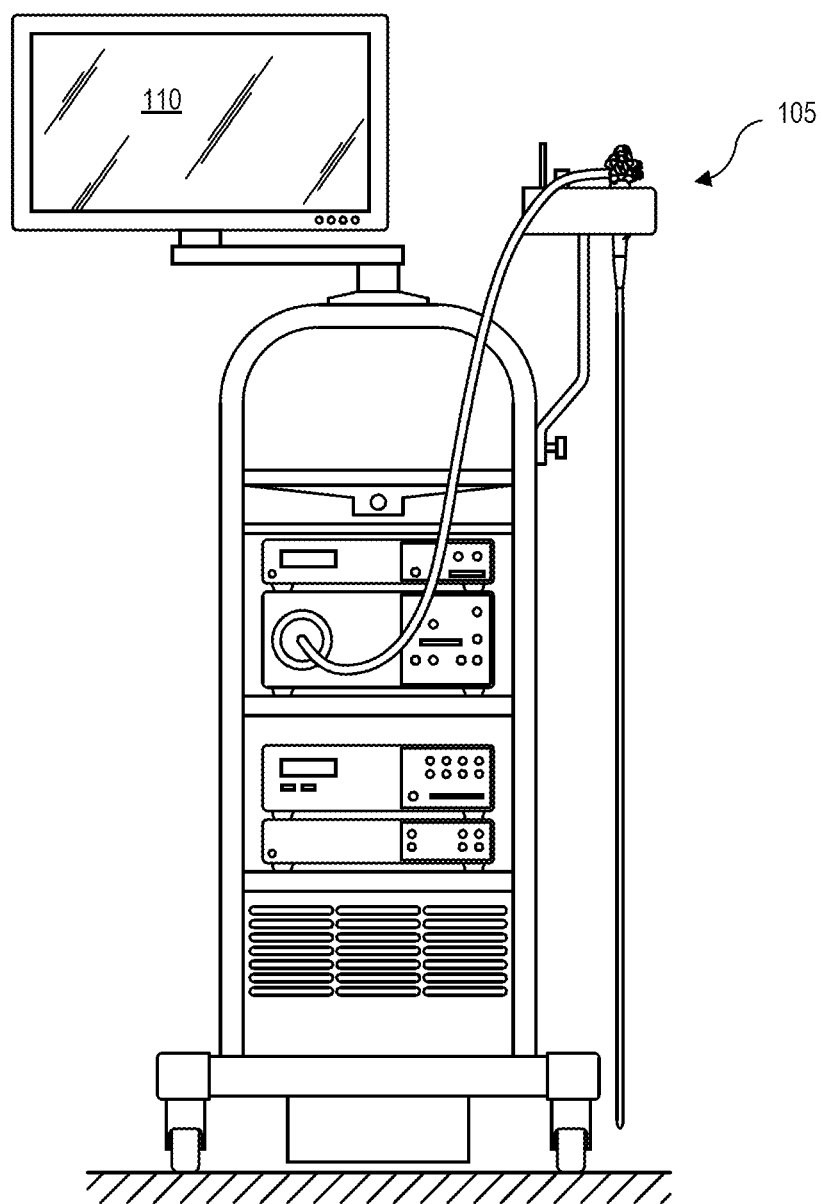
FIG. 1A illustrates a colonoscopy tower system, in accordance with an embodiment of the disclosure.

Embodiments of a system, apparatus, and method for a user-interface (UI) to aid navigation of an endoscopy (particularly colonoscopy) procedure are described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Conventional endoscopy and colonoscopy interfaces only display the live video feed on the screen without providing any other user aids. Embodiments of the endoscopy user-interfaces (UIs) described herein introduce additional on-screen elements to support and aid the endoscopist fully visualize every surface patch of a tubular anatomical structure (e.g., colon) and navigate the endoscopy procedure (e.g., colonoscopy). These visualization and navigational aids improve polyp detection and the reliability of the overall endoscopy procedure. The user-interfaces presented below are described in specific relation to colonoscopes and colonoscopy procedures performed within the lumen of a colon; however, it should be appreciated the user-interfaces are more generally applicable to endoscopes and endoscopy procedures performed within the lumen of any tubular anatomical structure including non-gastroenterological structures such as the esophagus, bronchial tubes, etc. Specific instances of the terms "colonoscopy", "colonoscope", or "colon" may be swapped throughout the detailed description for their more generic counterparts "endoscopy", "endoscope", or "tubular anatomical structure," respectively.

In certain embodiments, machine learning (ML) models may be used to determine and track relative position, depth, and viewing angle of a distal tip of the colonoscope camera within a colon. Examples of these image analysis techniques are described in *"Detecting Deficient Coverage in Colonoscopies," Freedman et al., IEEE Transactions On Medical Imaging, Vol. 39, No. 11, November* 2020. ML models may further be trained to provide polyp detection and/or optical biopsies. Position, depth, angle, direction, and speed of the endoscope along with feature detection (polyp detection), optical biopsies, and surface patch coverage tracking may all be performed based upon image analysis of the video output from the colonoscope using an ML-based visual odometry. In other embodiments, additional/alternative position sensors or real-time scanning techniques may be implemented to obtain position/depth tracking information of the distal end of the colonoscope.

The data obtained from the above image analysis of a live video feed from a colonoscope may be leveraged to display a number of beneficial on-screen visual aids in a colonoscopy UI. These visual aids provide improved operator context and visualization of the colonoscopy procedure. For example, these aids may include a navigational map that depicts longitudinal sections of a colon, a position marker indicating a position of a field of view (FOV) of a camera capturing the live video feed, annotations indicating inspection status of different longitudinal sections of a colon, a cross-sectional coverage map indicating whether portions or surface patches of a longitudinal section have been adequately inspected, guidance arrows prompting the endoscopist back to a longitudinal section deemed inadequately inspected, annotations highlighting detected polyps, and display of a variety of other valuable feedback data (e.g., estimated withdrawal time, polyp detected status, polyp detected history, important notifications, etc.). It should be appreciated that the terms "annotate" or "annotation" are broadly defined herein to include both textual markups (e.g., on screen textual prompts or dialog) and graphical/pictorial markups (e.g., on screen boxes, arrows, shading, coloring, highlighting, etc.).

In addition (or alternatively) to the above context aware visual aids, other navigational aids (i.e., onscreen widgets) may provide a sort of navigational context. These navigational aids include an observation location map depicting a point of observation from which the live video feed is acquired within the lumen relative to a cross-sectional depiction of the lumen, a velocity indicator depicting real-time direction of motion and magnitude of motion through the lumen, and a visibility indicator indicating a proportion of interior surface area of the tubular anatomical structure (e.g., colon wall) surrounding the lumen that was viewable versus unviewable in the live video feed as the colonoscope camera traverses different longitudinal sections of the colon.

Providing these visual aids on the colonoscopy UI in real-time and contemporaneously alongside the live video feed from the colonoscope provides a higher level of context and orientation to the endoscopist. The visual aids increase confidence that all surface patches of the tubular anatomical structure e.g., the internal surfaces of the colon wall) have been reviewed or provide actionable, real-time feedback to timely inform the endoscopist to retrace a section of the colon. Ultimately, the visual aids improve the operator experience thus providing improved detection of polyps and improved confidence in the overall colonoscopy procedure.

Figure 1B:
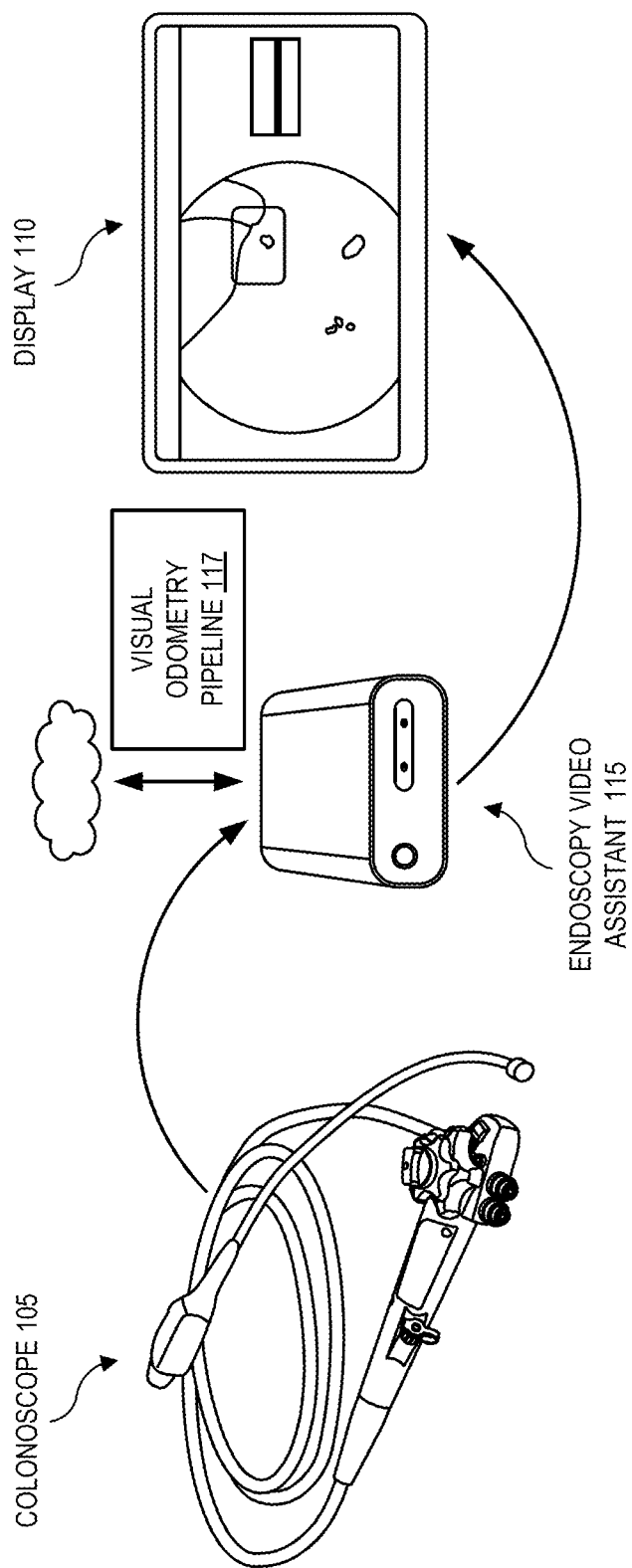
FIG. 1B illustrates an endoscopy video assistant capable of generating a colonoscopy user-interface including a live video feed and various visual aids during a colonoscopy procedure, in accordance with an embodiment of the disclosure.

FIG. 1A illustrates a colonoscopy tower system 100, in accordance with an embodiment of the disclosure. System 100 illustrates an example hardware system in which embodiments of the improved colonoscopy UIs described herein may be used. System 100 includes a colonoscope 105 (or generically an endoscope) coupled to a display 110 for capturing images of a colon (generically a tubular anatomical structure) and displaying a live video feed of the colonoscopy (endoscopy) procedure. In one embodiment, the image analysis and UI overlays described herein may be performed and generated by a processing box that plugs in between the colonoscope 105 and display 110. FIG. 1B illustrates an example endoscopy video assistant (EVA) 115 capable of generating the colonoscopy UIs described herein.

EVA 115 may include the necessary processing hardware and software, including ML models and/or visual odometry pipeline 117 to perform the real-time image processing, analysis, and UI overlays. For example, EVA 115 may include a data storage, a general-purpose processor, a graphics processor, and video input/output (I/O) interfaces to receive a live video feed from colonoscope 105 and output the live video feed within a UI that overlays various visual aids and data. In some embodiments, EVA 115 may further include a network connection for offloading some of the image processing and/or reporting and saving coverage data for individual patient recall and/or longitudinal, anonymized studies. For example, visual odometry pipeline 117 may include software components (e.g., ML models) to perform position, depth, angle analysis along with feature identification and tracking on the live video feed. Visual odometry pipeline 117 may be entirely executed on EVA 115, partially offloaded from EVA 115 to cloud computing nodes, or potentially entirely offloaded to remote computing nodes if bandwidth permits. Implementation details of an example visual odometry pipeline 117 are described in "*Detecting Deficient Coverage in Colonoscopies,*" Freedman et al., IEEE Transactions On Medical Imaging, Vol. 39, No. 11, November 2020.

The colonoscopy UI may include the live video feed reformatted, parsed, or scaled into a video region (e.g., video region 205 in FIGS. 2 and 5), or may be a UI overlay on top of the existing colonoscopy monitor feed to maintain the original format, resolution, and integrity of the colonoscopy live video feed as well as reduce latency.

Figure 2:
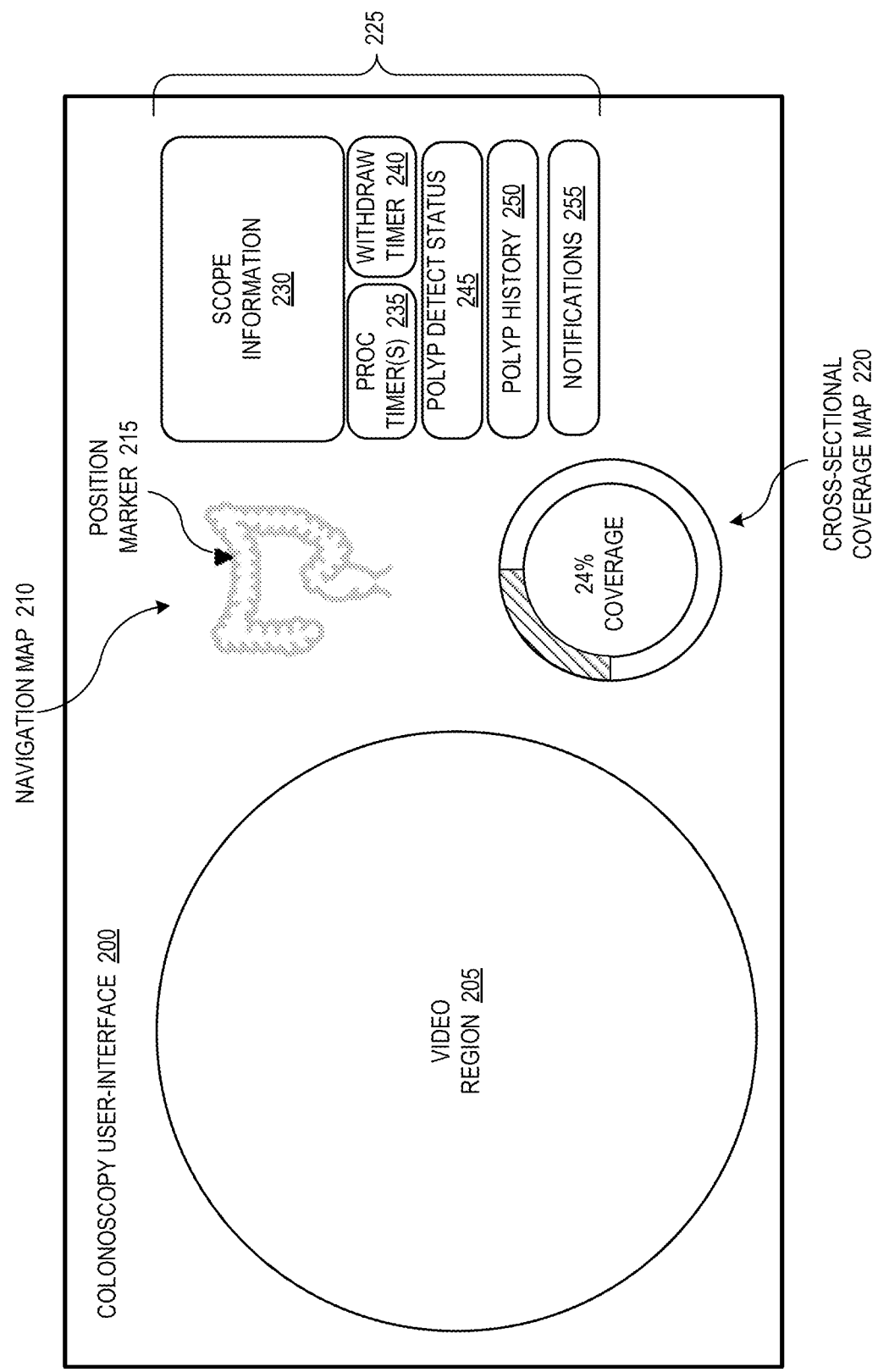
FIG. 2 illustrates a colonoscopy user-interface for aiding visualization of a colonoscopy procedure, in accordance with an embodiment of the disclosure.

FIG. 2 illustrates a colonoscopy UI 200 for visualizing a colonoscopy procedure, in accordance with an embodiment of the disclosure. The illustrated embodiment of colonoscopy UI 200 includes a video region 205 for displaying a live video feed, a navigation map 210 with a position marker 215, a cross-sectional coverage map 220, and a region for procedure data 225. The illustrated embodiment of procedure data 225 includes scope information 230, procedure timer(s) 235, a withdrawal timer 240, a polyp detected status 245, polyp detected history 250, and notifications 255.

As mentioned, video region 205 provides a region within colonoscopy UI 200 to display a live video feed of the interior of a colon captured during a colonoscopy procedure by a camera of colonoscope 105. In other words, video region 205 may be used to display the real-time FOV captured by the camera of colonoscope 105, which acquires its video from the distal tip of colonoscope 105. Although video region 205 is illustrated as having a round FOV, in other embodiments, the FOV may be rectangular, square, or otherwise.

Navigation map 210 depicts longitudinal sections of the colon. Each longitudinal section represents a different depth (z-axis) into the colon (or large intestine) extending from the rectum or anal canal to the cecum. Navigation map 210 may be implemented as an anatomical atlas or caricature being representative of the colon, or an actual three-dimensional (3D) model of the colon. In the case of a 3D model, the 3D model of the colon may be generated during an insertion phase of the colonoscopy procedure as colonoscope 105 is inserted into the anal canal and moved towards the cecum. The live video feed during insertion may be analyzed and mapped into the 3D model. In the illustrated embodiment, navigation map 210 is annotated with position marker 215 to indicate a longitudinal position of the FOV of the live video feed and by extension the longitudinal position of the distal end of colonoscope 105 within the colon. In one embodiment, position marker 215 does not appear on navigation map 210 until after the colon has been fully mapped or traversed during the insertion phase. After the insertion phase, position marker 215 moves in real-time tracking the position of the distal end of colonoscope 105 and the FOV of the live video feed during the withdrawal phase.

Figures 3A, 3B:
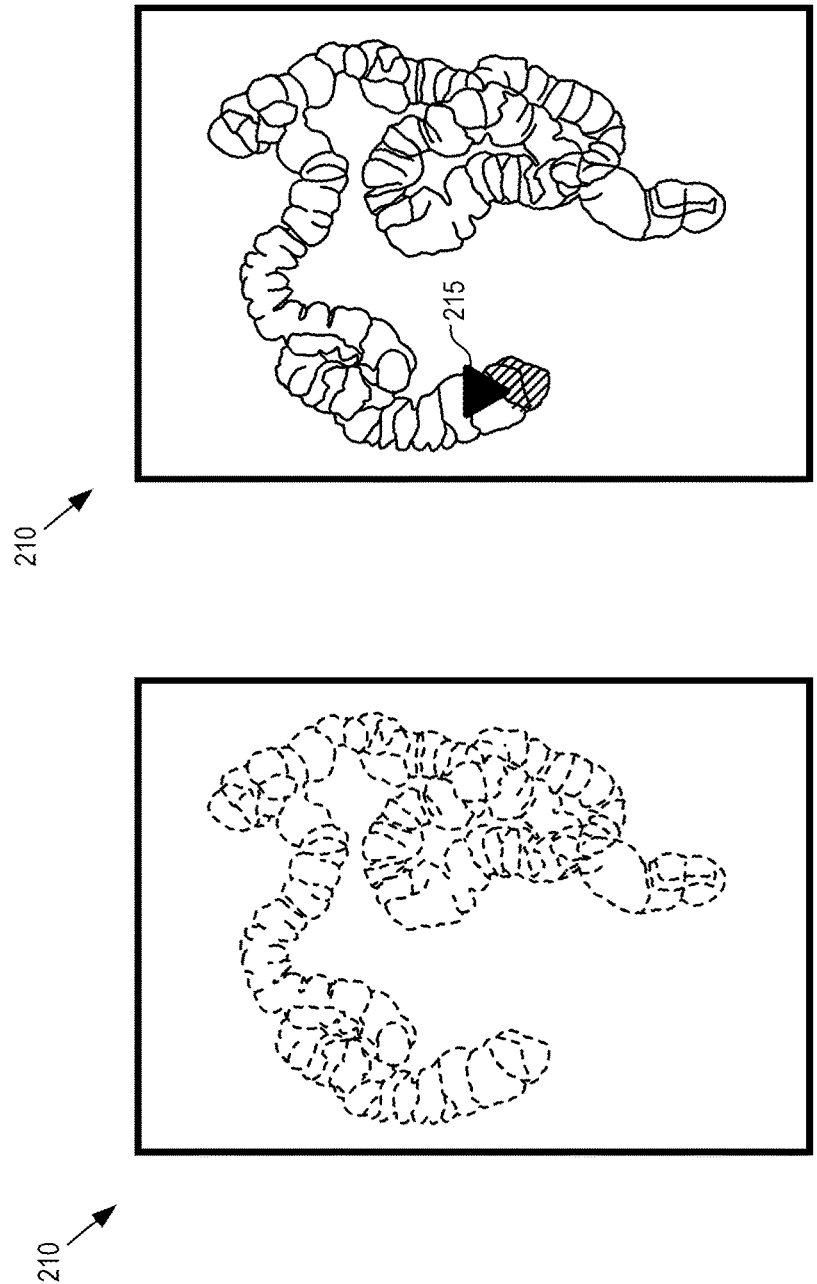
FIGS. 3A, B, C, and D illustrate a navigational map of a colon with coverage annotations and a position marker to aid a colonoscopy procedure, in accordance with an embodiment of the disclosure.

FIGS. 3A-D illustrate further details of navigational map 210, in accordance with an embodiment of the disclosure. As illustrated in FIG. 3A, navigational map 210 may be initially presented in a lighter shade or grayed out shade during the insertion phase of the colonoscopy procedure. In yet other embodiments, navigational map 210 may not be initially presented until the end of the insertion phase or beginning of the withdrawal phase. The insertion phase may be deemed complete once the cecum is reached and recognized as the end of the colon. The colon illustration may be withheld, grayed out, or presented in a lighter shade while the colon is being spatially mapped during the insertion phase. The spatial mapping may be achieved using a 3D visual mapping via image analysis of the live video feed during the insertion phase. In other embodiments, additional sensors and/or tracking devices may be used (alone or in conjunction with the image analysis) to facilitate spatial mapping or generation of a full 3D model of the colon. For example, ultrasound imaging, magnetic tracking, etc. may be used to track the distal tip of colonoscope 105 as it progresses through the colon. Preoperative imaging may also be analyzed when mapping the colon.

In FIG. 3B, upon commencement of the withdrawal phase, navigation map 210 is fully presented and position marker 215 displayed. Navigation map 210 along with position marker 215 present the endoscopist with a visual representation of the position of the FOV of the live video feed within the colon along with a visual estimation of the remaining distance to traverse during the withdrawal phase.

Referring to FIGS. 3C and 3D, as colonoscope 105 is withdrawn through the colon, navigation map 210 is annotated to illustrate the inspection status of each longitudinal section along the way. This annotation may be updated in real-time during the withdrawal phase. Longitudinal sections deemed fully inspected (i.e., all surface patches in those longitudinal sections have been adequately inspected) are annotated as such. For example, longitudinal sections that are deemed adequately inspected may be colored green (FIG. 3C). Correspondingly, if the endoscopist withdrawals through a given longitudinal section without fully inspecting every surface patch within that longitudinal section, then the corresponding longitudinal section on navigation map 210 is annotated to represent an inadequate inspection. For example, the inadequately inspected section may be colored red (FIG. 3D) to indicate that one or more surface patches of the colon in the longitudinal section has been deemed inadequately inspected. Of course, other colors, shades, or labels may be used to indicate adequate or inadequate inspection of a given longitudinal section.

Returning to FIG. 2, the illustrated embodiment of colonoscopy UI 200 further includes a cross-sectional coverage map 220. Cross-sectional coverage map 220 indicates whether angular portions of a cross-section of a given longitudinal section of the colon are deemed adequately or inadequately inspected. For example, cross-section coverage map 220 may display a cross-sectional map of the current longitudinal section indicated by position marker 215. In the illustrated embodiment, cross-sectional coverage map 220 is indicating that only the surface patch of the colon residing in the upper left quadrant of the current longitudinal section has been adequately inspected and the remaining 76% of the perimeter surface patches of the current longitudinal section have not yet been adequately inspected. During the insertion phase, the image inspection software (e.g., trained neural networks) maps and orients itself to the colon. During the withdrawal phase, cross-sectional coverage map 220 may map surface patch inspection status relative to the frame of reference of the FOV of the camera during the insertion phase. In other embodiments, cross-sectional coverage map 220 maps surface patch inspections relative to a current frame of reference or other anatomical reference frames (e.g., sagittal, coronal, or median planes).

Figure 4:
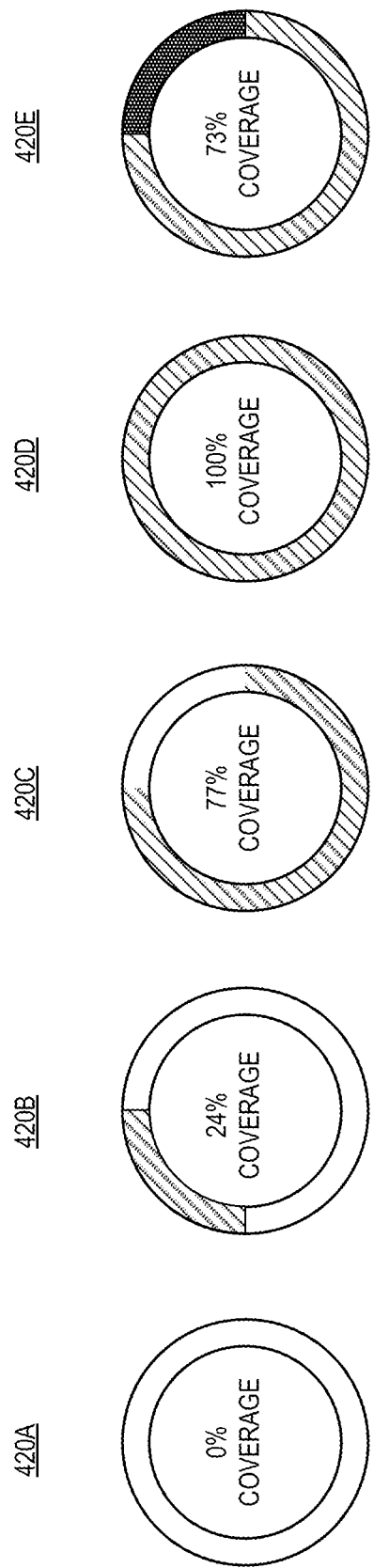
FIG. 4 illustrates a cross-sectional coverage map indicating whether angular portions of a cross-section of a given longitudinal section of a colon are deemed adequately or inadequately inspected, in accordance with an embodiment of the disclosure.

Turning to FIG. 4, as the endoscopist commences withdrawal through a longitudinal section of the colon, cross-sectional coverage map 420A initially displays 0% inspection coverage. While loitering in and inspecting surface patches of a given longitudinal section, EVA 115 tracks the inspection and begins to highlight cross-sectional coverage map 420B to reflect an estimated inspection coverage. As the endoscopist continues to inspect a given longitudinal section, more of the circle of cross-sectional coverage map 420C is highlighted until all surface patches of the current longitudinal section are deemed inspected, as represented by cross-sectional coverage map 420D showing 100% inspection coverage. As colonoscope 105 is withdrawn to the next longitudinal section, the inspection status is reset to 0% and the process repeats. If colonoscope 105 is withdrawn past a longitudinal section before that section is fully inspected, when the endoscopist returns to the missed longitudinal section for reinspection, cross-sectional coverage map 420E highlights (e.g., colored red) the missed area to quickly guide the endoscopist to the missed location/surface patch (es).

The inspection status may be determined or estimated using a combination or weighting of one or more of the following factors: (a) loitering time of a camera of colonoscope 105 within the given longitudinal section; (b) a determination of whether all surface patches of the colon within the given longitudinal section is observed by the camera (e.g., sweeps within the FOV of the camera for a threshold period of time); (c) a distance between each of the surface patches and the camera when each of the surface patches is observed by the camera; (d) an angle of viewing incidence between the camera and each of the surface patches when each of the surface patches is observed by the camera, or (e) an ML analysis of the colonoscopy video to determine whether any scene potentially included an anatomical fold or area where additional colon anatomy may have be hidden from the FOV. The distance and viewing angles may be thresholded such that surface patches that technically sweep into the FOV of the camera but are either too far away or occur at too steep of an angle may be deemed to not have been adequately observed even though the surface patch did pass within the FOV of the camera. When operating within threshold limits for viewing distance and angle of viewing incidence, loitering times may be adjusted depending upon the actual viewing distance and/or angle of viewing incidence. For example, a viewing distance that does not exceed a threshold maximum may still require twice the loitering time if its distance is considered longer than typical, but does not exceed a maximum distance permitted. Yet another factor that may be considered when determining inspection status is image quality while observing a given surface patch, which may include focus, contrast, sharpness or other image quality characteristics. Again, permissible thresholds may be enforced and loitering multipliers applied for sub-optimal conditions when observing a given surface patch. In some embodiments, any or all of the above factors may be used as ground truth data when training an ML model to estimate or otherwise "deem" an longitudinal section as adequately or inadequately inspected.

In one embodiment, cross-sectional coverage map 220 (or 420A-420D) may visually indicate the angular portions observed/not observed for a given longitudinal section. In this manner, the endoscopist is quickly guided as to which perimeter surface patches still need to be observed for a given depth or longitudinal position. In yet another embodiment, cross-sectional coverage map 220 is merely an overall percentage estimate of the surface patches observed within a longitudinal section without specifically connoting angular directions of observed and unobserved portions.

Returning to FIG. 2, colonoscopy UI 200 includes a region for displaying procedure data 225. The illustrated embodiment of procedure data 225 includes scope information 230, procedure timer 235, withdrawal timer 240, polyp detected status 245, polyp detected history 250, and notifications 255. Scope information 230 may include metadata pertinent to the particular colonoscope 105 such as camera resolution, software/firmware version, frame rate, color space, etc.

Procedure timer(s) 235 may include one or more timers that track the overall procedure time since commencement of the insertion phase, track the procedure time of just the insertion phase, or track the procedure time since commencement of the withdrawal phase. Withdrawal timer 240 displays an estimated withdrawal time to complete the withdrawal phase of the colonoscopy procedure. The estimated withdrawal time may be calculated using a trained neural network upon inspecting the colon during the insertion phase and may further be updated as the withdrawal phase progresses. As such, the estimated withdrawal time may not be displayed until after completion of the insertion phase and represents a sort of countdown timer until completion of the withdrawal phase.

Polyp detect status 245 represents an indication of whether the image analysis and polyp detect software has detected a polyp in the current FOV or live image feed currently displayed in video region 205. If a polyp is detected in live video feed, then the detected polyp may be highlighted or accentuated with an annotation clearly identifying its location within the displayed image. The annotation may be implemented using a variety of different outline shapes, colors, shadings, labels, etc.

Polyp detected history 250 represents a count of the overall number of detected polyps. Additionally, polyp detected history 250 may include a selectable menu for displaying further information regarding the particular detected polyps. For example, if an ML classifier is applied to perform optical biopsies on the detected polyps, then the results of the optical biopsy may be accessed via the polyp detected history 250 by selecting a given polyp. The results may include a classification of benign, precancerous, cancerous, etc. along with display of a confidence interval. In yet other embodiments, reference images of polyps corresponding to the classification of a polyp may be linked and presented upon selection so that the endoscopist may compare the live video feed image (or static screen capture image thereof) against a reference image during real-time observation of a given polyp. Finally, procedure data 225 may further include a section for notifications 255 where miscellaneous notifications including polyp types/classifications may also be presented.

Embodiments disclosed herein provide a colonoscopy UI 200 that contemporaneously presents the live video feed from colonoscope 105 alongside contextual/orientational data from navigation map 210, cross-sectional coverage map 220, and procedure data 225. These contemporaneous visual aids provide a higher level of context and orientation to the endoscopist, thereby improving the reliability of the colonoscopy procedure and confidence that all polyps are detected.

Figure 5:
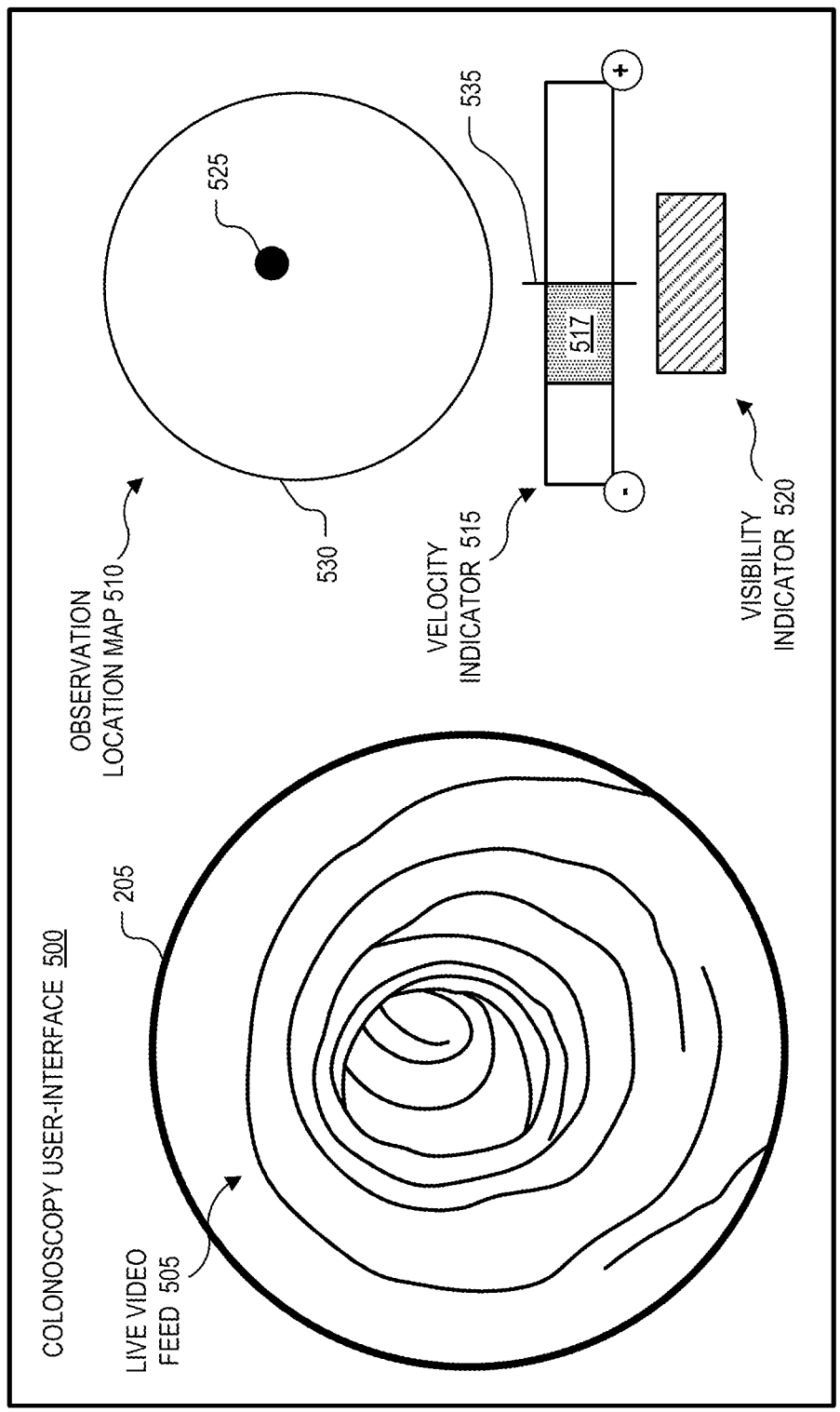
FIG. 5 illustrates a colonoscopy user-interface for aiding navigation of a colonoscope during a colonoscopy procedure, in accordance with an embodiment of the disclosure.

FIG. 5 illustrates a colonoscopy UI 500 for aiding navigation of colonoscope 105 during a colonoscopy procedure, in accordance with an embodiment of the disclosure. The illustrated embodiment colonoscopy UI 500 includes video region 205 for displaying live video feed 505, an observation location map 510, a velocity indicator 515, and a visibility indicator 520.

The contextual aids of UI 200 and the navigational aids of UI 500 may be selected/configured by the clinician or endoscopist. For example, the endoscopist may switch between UIs 200 and 500 on-demand during a colonoscopy procedure. In yet another embodiment, the various on-screen widgets (e.g., navigation map 210, cross-sectional coverage map 220, procedure data 225, observation location map 510, velocity indicator 515, or visibility indicator 520) may be intermingled or adjusted according the endoscopist's preferences and paired in various combinations for contemporaneous display along side live video feed 505.

Observation location map 510 depicts a point of observation from which live video feed 505 is acquired by colonoscope 105 within the lumen of a tubular anatomical structure. The lumen is the inside space of the tubular anatomical structure. Example tubular anatomical structures include a colon, an intestine, an esophagus, bronchial tubes, etc. Observation location map 510 depicts the point of observation of live video feed 505 relative to a cross-sectional depiction of the lumen as the endoscope moves longitudinally along the tubular anatomical structure within the lumen. Longitudinal movement is z-axis movement along the longitudinal axis of the tubular anatomic structure. In contrast, observation location map 510 resides in the x-y plane of the lumen, which is perpendicular to the z-axis.

In the illustrated embodiment, observation location map 510 includes an observation point marker 525 disposed within a cross-sectional depiction 530 of the lumen. Observation point marker 525 represents the point of observation of the distal tip of colonoscope 105 while cross-sectional depiction 530 represents the localized cross-section of the lumen in the vicinity of the distal tip. Although FIG. 5 illustrates cross-sectional depiction 530 as a circle, in other embodiments, the cross-sectional depiction 530 may be an oval, ellipse, off-circle shape, irregular shape, or otherwise. Cross-sectional depiction 530 may correspond to the actual cross-sectional shape of the lumen, or represent a rough approximation of the cross-sectional shape. As an example, FIG. 5 presents observation point marker 525 as indicating that live video feed 505 is being captured by colonoscope 105 having its distal tip close to center within the lumen, but with a slight upward-right positional bias.

In the illustrated embodiment, observation location map 510 is contemporaneously presented within UI 500 proximate to live video feed 505 to provide real-time navigation context with live video feed 505. Observation location map 510 helps the clinician better understand live video feed 505 and the perspective from which the images are captured. This perspective or observation location relative to the cross-section of the lumen may be particularly helpful in longitudinal sections of a colon or other tubular anatomical structure that are particularly curvy or folded on themselves.

Figure 6:
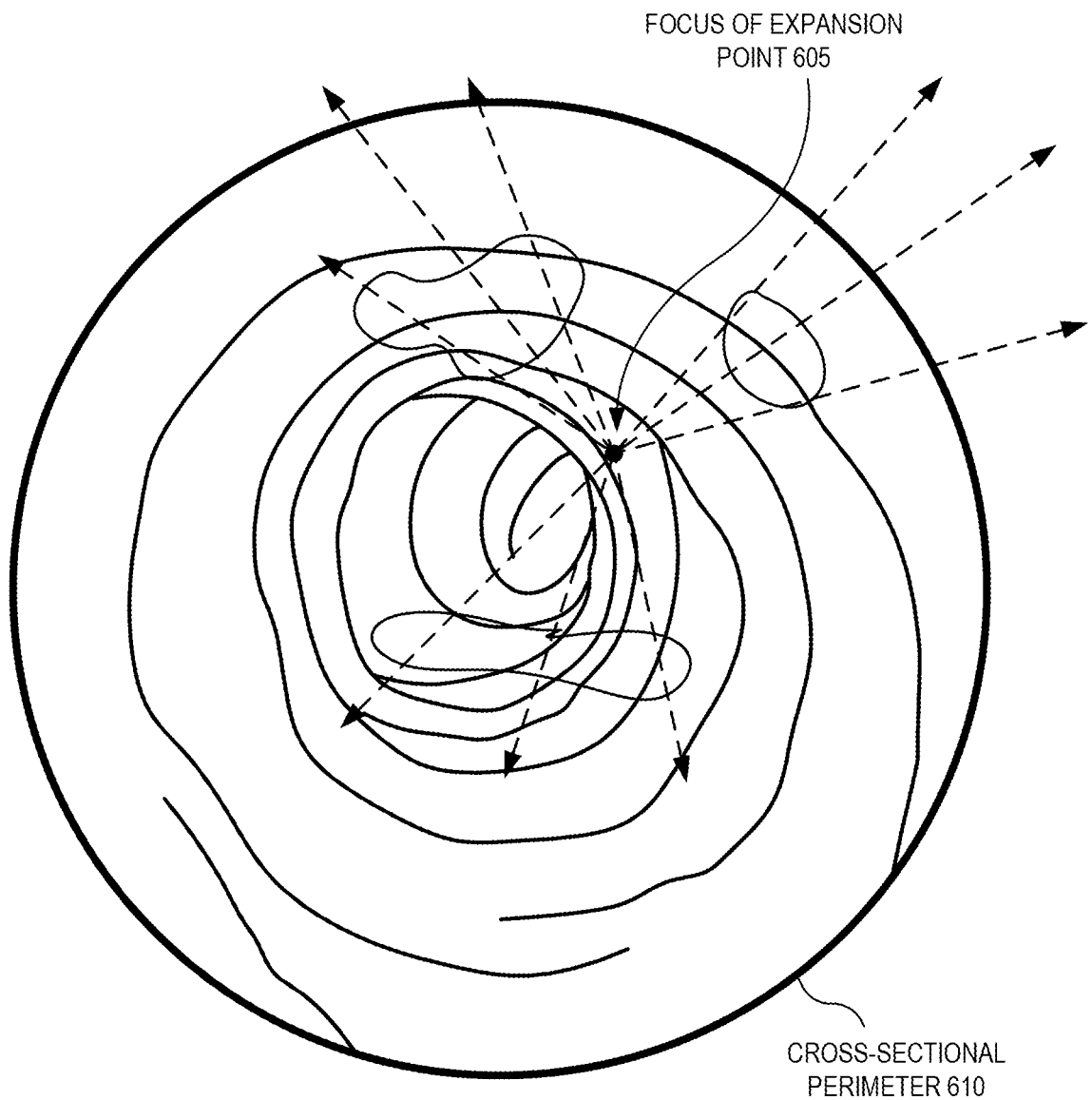
FIG. 6 illustrates how a point of observation may be determined with respect to a lumen cross-section, in accordance with an embodiment of the disclosure.

FIG. 6 illustrates how a point of observation may be determined with respect to a lumen cross-section, in accordance with an embodiment of the disclosure. In the illustrated embodiment, a focus of expansion point 605 is extracted from consecutive images of live video feed 505. While colonoscope 105 is moved along the tubular anatomical structure the optical flow field for the moving observer (i.e., the colonoscope camera) expands from a singular point, referred to as the "focus of expansion," which is illustrated as focus of expansion point 605. In other words, if the tubular anatomical structure is assumed to be substantially still while the distal tip of colonoscope 105 is inserted or withdrawn through the lumen, then the movement or velocity vectors associated with each image pixel between consecutive images of live video feed 505 can be extended to intersect at a single point in the image referred to as focus of expansion point 605. In one embodiment, focus of expansion point 605 is used to generate point of observation 525 within observation location map 510. Furthermore, image analysis (e.g., feature detection) may be executed on live video feed 505 to identify the cross-sectional perimeter 610 of the lumen. The relative position of focus of expansion point 605 compared to the cross-sectional perimeter 610 may then be used to generate observation location map 510.

Returning to FIG. 5, colonoscopy UI 500 further includes velocity indicator 515. Velocity indicator 515 visually depicts in real-time a direction of longitudinal motion of colonoscopy 105 moving through the lumen along with a magnitude of that longitudinal motion. Velocity indicator 515 may be generated based solely on optical flow analysis (e.g., motion tracking) of features or pixels in live video feed 505. In other embodiments, additional sensors may be positioned on colonoscope 105 and/or around the body to track motion of the distal tip of colonoscope 105. Velocity indicator 515 may be contemporaneously presented proximate to live video feed 505 within colonoscopy UI 500 to provide real-time navigational context with live video feed 505.

In the illustrated embodiment, velocity indicator 515 includes a dynamic bar graph 517 that extends in a positive or negative direction from a zero point 535 based upon the direction and magnitude of motion of colonoscope 105. For example, as colonoscope 105 is withdrawn through the tubular anatomical structure, dynamic bar graph 517 extends in the negative direction from zero point 535. As the rate or speed of withdrawal increases, dynamic bar graph 517 would grow or extend further in the negative direction. Correspondingly, as colonoscope 105 is inserted through the tubular anatomic structure, dynamic bar graph 517 would extend in the positive direction with its length corresponding to the magnitude of insertion motion along the z-axis. In the example of FIG. 5, colonoscope 105 is depicted as being withdrawn at a moderate rate.

Colonoscopy UI 500 further includes visibility indicator 520. Visibility indicator 520 indicates a proportion of interior surface area of the tubular anatomical structure (e.g., colon wall) that was viewable versus unviewable in live video feed 505 as colonoscope 105 traverses a longitudinal section of the tubular anatomical structure. Visibility indicator 520 may be contemporaneously presented proximate to live video feed 505 within colonoscopy UI 500 to provide real-time, actionable navigation context with live video feed 505. In particular, visibility indicator 520 operates to convey a simple, easy to understand message to the endoscopist whether or not they have misses missed inspecting too much interior surface area while traversing the tubular anatomical structure. The message is intended to provide real-time actionable feedback, so the endoscopist can stop and move back to a longitudinal section just missed as opposed to providing a summary at the end of the procedure.

In one embodiment, the proportion of interior surface area of the tubular anatomical structure that was viewable versus unviewable is based upon a temporal integration window (i.e., a sliding window in time) ranging between 5 secs to 30 seconds. In other words, visibility indicator 520 indicates the percentage of interior surface patches that were recently viewable versus hidden from the FOV of colonoscope 105. In one embodiment, a 10 second window is thought to be an appropriate temporal integration window that balances a meaningful integration window that is small enough to provide actionable feedback while not being so small as to provide spurious feedback.

While visibility indicator 520 may provide feedback as a numerical value, in other embodiments, visibility indicator 520 provides feedback in the form of discretized ranges. For example, the proportion of viewable versus unviewable interior surface area may be categorized into two, three, or four ranges (e.g., four or less ranges). In one example, three discrete ranges may be color coded as follows: green corresponding to "mostly viewed" (100% to 75% viewable), yellow corresponding to "partially viewed" (75% to 50% viewable), and red corresponding to "much unviewed" (50% to 0%). Of course, these numerical ranges, colors, and descriptive phrases are merely demonstrative and other colors, annotations, descriptions, or numerical ranges may be implemented.

Figure 7A:
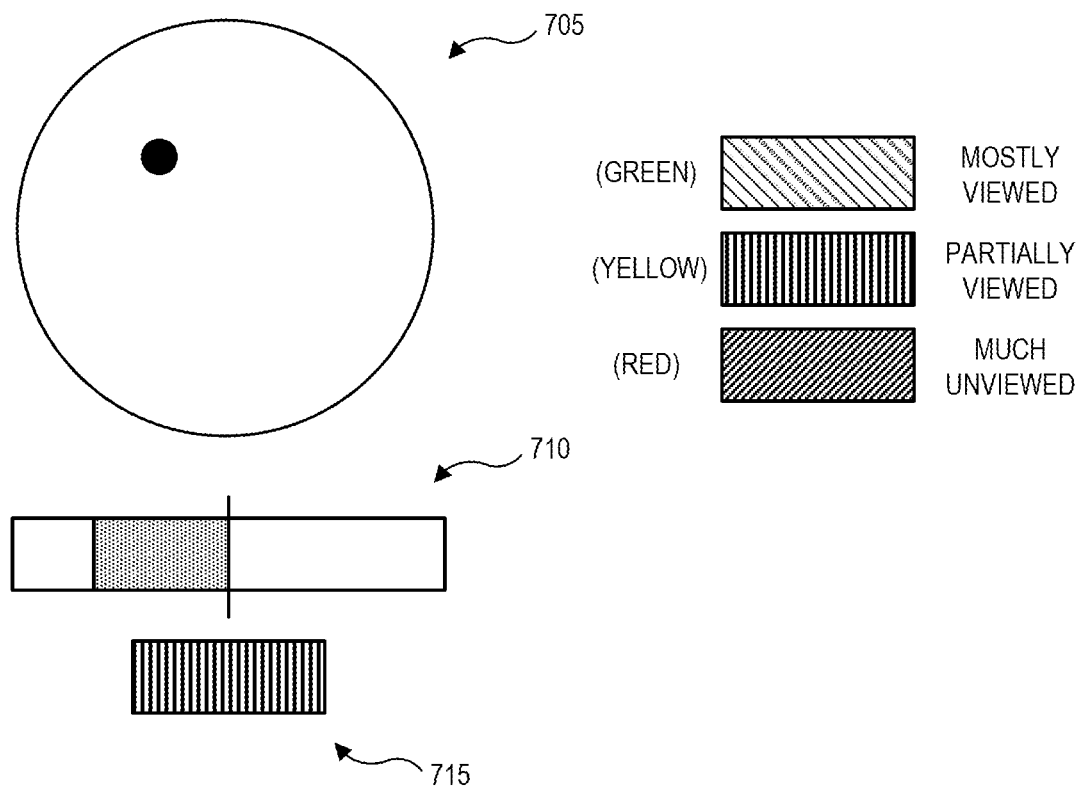
FIGS. 7A & 7B illustrate examples of navigational aids during a colonoscopy procedure, in accordance with an embodiment of the disclosure.
Figure 7B:
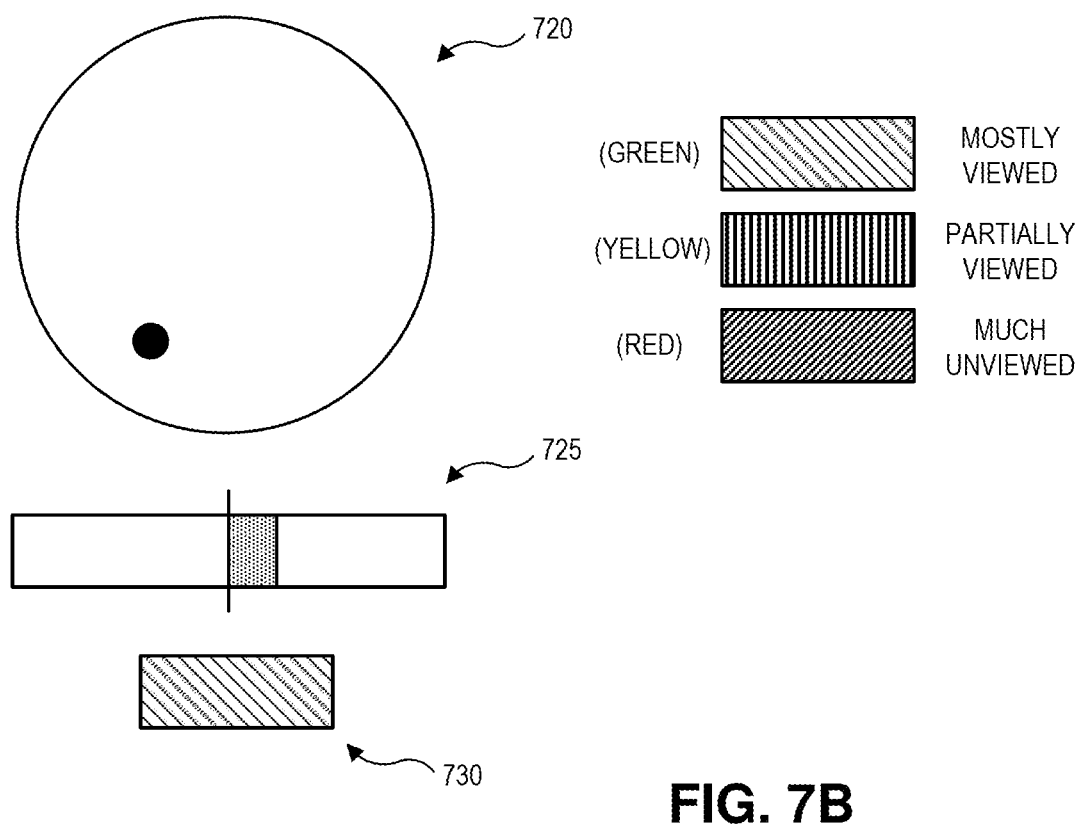

FIGS. 7A & 7B illustrate examples of navigational aids presented contemporaneously with live video feed 505 during a colonoscopy procedure, in accordance with an embodiment of the disclosure. FIG. 7A illustrates a scenario where the distal end of colonoscope 105 is observing the lumen from an upper-left quadrant of the lumen as conveyed by observation location map 705. Colonoscope 105 is being withdrawn at a relatively quick pace as conveyed by velocity indicator 710 and visibility indicator 715 is color coded yellow to indicate that the most recently traversed portion of the colon was "partially viewed," meaning some surface patches were missed based upon coverage analysis of live video feed 505 by EVA 115. FIG. 7B illustrates a scenario where the distal end of colonoscope 105 is observing the lumen from a lower-left quadrant of the lumen as conveyed by observation location map 720. Colonoscope 105 is being inserted at a relatively slow pace as conveyed by velocity indicator 725 and visibility indicator 730 is color coded green to indicate that the most recently traversed portion of the colon was "mostly viewed," meaning few to no surface patches were unviewable based upon analysis of live video feed 505 by EVA 115. In the case of a colonoscopy, the visibility indicator may only be presented during the withdrawal phase of the colonoscopy; however, in the general case of an endoscopy procedure inspecting any tubular anatomical structure, it is anticipated that the visibility indicator may be applicable during both insertion and withdrawal phases.

The above user-interfaces have been described in terms of a colonoscopy and is particularly well-suited as a colonoscopy user-interface to aid visualization and navigation of colonoscopy procedures. However, it should be appreciated that UIs 200 or 500 may be more broadly/generically described as endoscopy UIs that may be used to visualize and navigate endoscopy procedures, in general, related to other tubular anatomical structures. For example, the UIs are applicable to aid visualization and navigation of other gastroenterological procedures including endoscopy procedures within the upper and lower gastrointestinal tracts. In yet other examples, UIs 200 and 500 may be used to visualize exploratory endoscopy procedures of non-gastroenterological structures such as the esophagus, bronchial tubes, or other tube-like anatomical structures. When adapting the user-interfaces to visualize/navigate other endoscopy procedures, navigational map 210 may represent a map of the corresponding anatomical structure being explored, cross-sectional coverage map 220 may represent cross-sectional or perimeter inspection coverage of the corresponding anatomical structure, and observation location map 510 may include a cross-sectional depiction of the corresponding anatomical structure.

Figure 8:
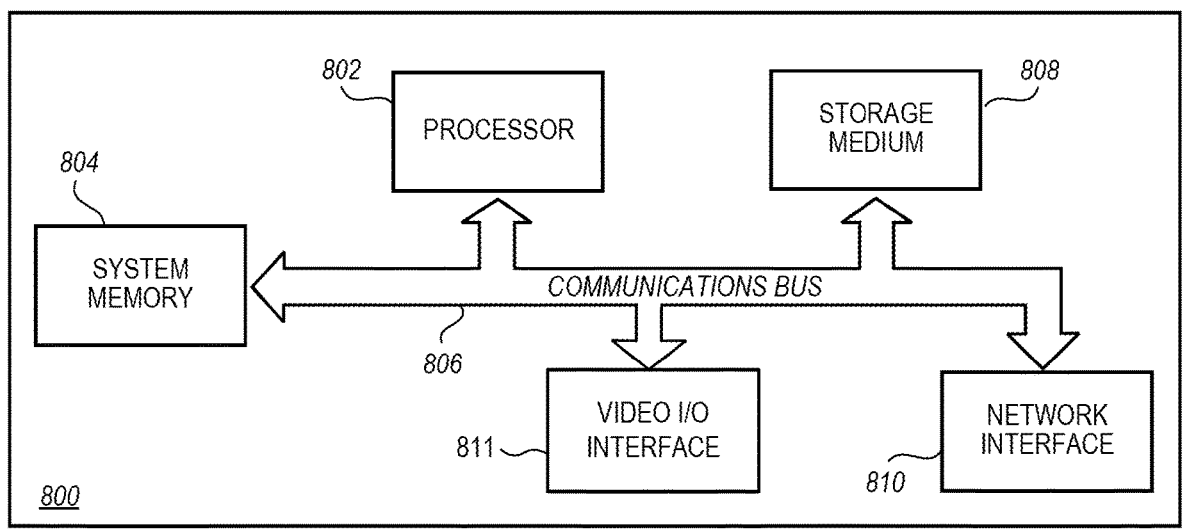
FIG. 8 is a functional block diagram illustrating a demonstrative computing device for implementing an endoscopy video assistant, in accordance with any embodiment of the disclosure.

FIG. 8 is a block diagram that illustrates aspects of a demonstrative computing device appropriate for implementing EVA 115, in accordance with embodiments of the present disclosure. Those of ordinary skill in the art will recognize that computing device 800 may be implemented using currently available computing devices or yet to be developed devices.

In its most basic configuration, computing device 800 includes at least one processor 802 and a system memory 804 connected by a communication bus 806. Depending on the exact configuration and type of device, system memory 804 may be volatile or nonvolatile memory, such as read only memory ("ROM"), random access memory ("RAM"), EEPROM, flash memory, or similar memory technology. Those of ordinary skill in the art will recognize that system memory 804 typically stores data and/or program modules that are immediately accessible to and/or currently being operated on by the processor 802. In this regard, the processor 802 may serve as a computational center of computing device 800 by supporting the execution of instructions.

As further illustrated in FIG. 8, computing device 800 may include a network interface 810 comprising one or more components for communicating with other devices over a network. Embodiments of the present disclosure may access basic services that utilize network interface 810 to perform communications using common network protocols. Network interface 810 may also include a wireless network interface configured to communicate via one or more wireless communication protocols, such as WiFi, 2G, 3G, 4G, LTE, WiMAX, Bluetooth, and/or the like.

In the exemplary embodiment depicted in FIG. 8, computing device 800 also includes a storage medium 808. However, services may be accessed using a computing device that does not include means for persisting data to a local storage medium. Therefore, the storage medium 808 may be omitted. In any event, the storage medium 808 may be volatile or nonvolatile, removable or nonremovable, implemented using any technology capable of storing information such as, but not limited to, a hard drive, solid state drive, CD-ROM, DVD, or other disk storage, magnetic cassettes, magnetic tape, magnetic disk storage, and/or the like.

The illustrated embodiment of computing device 800 further includes a video input/out interface 811. Video I/O interface 811 may include an analog video input (e.g., composite video, component video, VGG connector, etc) or a digital video input (e.g., HDMI, DVI, DisplayPort, USB-A, USB-C, etc.) to receive the live video feed from colonoscope 105 and another video output port to output the live video feed within colonoscopy UIs 200 or 500 to display 110. In one embodiment, video I/O interface 811 may also represent a graphics processing unit capable of performing the necessary computational video processing to generate and render colonoscopy UIs 200 or 500.

As used herein, the term "computer-readable medium" includes volatile and non-volatile and removable and non-removable media implemented in any method or technology capable of storing information, such as computer-readable instructions, data structures, program modules, or other data. In this regard, the system memory 804 and storage medium 808 depicted in FIG. 8 are merely examples of computer-readable media.

Suitable implementations of computing devices that include a processor 802, system memory 804, communication bus 806, storage medium 808, and network interface 810 are known and commercially available. For ease of illustration and because it is not important for an understanding of the claimed subject matter, FIG. 8 does not show some of the typical components of many computing devices. In this regard, the computing device 800 may include input devices, such as a keyboard, keypad, mouse, microphone, touch input device, touch screen, tablet, and/or the like. Such input devices may be coupled to computing device 800 by wired or wireless connections including RF, infrared, serial, parallel, Bluetooth, USB, or other suitable connection protocols using wireless or physical connections. Since these devices are well known in the art, they are not illustrated or described further herein.

The processes and user-interfaces described above are described in terms of computer software and hardware. The techniques described may constitute machine-executable instructions embodied within a tangible or non-transitory machine (e.g., computer) readable storage medium, that when executed by a machine will cause the machine to perform the operations described. Additionally, some of the processes or logic for implementing the user-interface may be embodied within hardware, such as an application specific integrated circuit ("ASIC") or otherwise.

A tangible machine-readable storage medium includes any mechanism that provides (i.e., stores) information in a non-transitory form accessible by a machine (e.g., a computer, network device, personal digital assistant, manufacturing tool, any device with a set of one or more processors, etc.). For example, a machine-readable storage medium includes recordable/non-recordable media (e.g., read only memory (ROM), random access memory (RAM), magnetic disk storage media, optical storage media, flash memory devices, etc.).

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. At least one non-transitory machine-accessible storage medium that provides instructions that, when executed by a machine, will cause the machine to perform operations comprising:
 generating an endoscopy user-interface for display on a screen during an endoscopy procedure;
 outputting a live video feed of a lumen of a tubular anatomical structure received from an endoscope during the endoscopy procedure for display within a video region of the endoscopy user-interface; and generating an observation location map for display within the endoscopy user-interface, wherein the observation location map depicts a point of observation from which the live video feed is acquired within the lumen relative to a cross-sectional depiction of the lumen as the endoscope moves longitudinally along the tubular anatomical structure within the lumen during the endoscopy procedure, wherein the cross-sectional depiction comprises a cross-sectional perimeter shape depiction of the lumen and the observation location map conveys a position of the point of observation relative to the cross-sectional perimeter shape depiction.

2. The at least one non-transitory machine-accessible storage medium of claim 1, wherein the cross-sectional depiction comprises a localized cross-section in a vicinity of a distal tip of the endoscope.

3. The at least one non-transitory machine-accessible storage medium of claim 1, wherein the observation location map is contemporaneously presented proximate to the live video feed within the endoscopy user-interface to provide real-time navigation context with the live video feed.

4. The at least one non-transitory machine-accessible storage medium of claim 1, wherein generating the observation location map comprises:
determining a focus of expansion point within the live video feed;
identifying a cross-sectional perimeter of the lumen in the live video feed; and
comparing a relative position of the focus of expansion point to the cross-sectional perimeter.

5. The at least one non-transitory machine-accessible storage medium of claim 1, further providing instructions that, when executed by the machine, will cause the machine to perform further operations, comprising:
generating a velocity indicator for display within the endoscopy user-interface, wherein the velocity indicator visually depicts in real-time a direction of longitudinal motion of the endoscope moving through the lumen and a magnitude of longitudinal motion of the endoscope moving through the lumen.

6. The at least one non-transitory machine-accessible storage medium of claim 5, wherein the velocity indicator comprises a dynamic bar graph that extends in a positive direction from a zero point to indicate a positive longitudinal motion of the endoscope moving through the lumen or extends in a negative direction from the zero point to indicate a negative longitudinal motion of the endoscope moving through the lumen.

7. The at least one non-transitory machine-accessible storage medium of claim 5, wherein the velocity indicator is contemporaneously presented proximate to the live video feed within the endoscopy user-interface to provide real-time navigation context with the live video feed.

8. The at least one non-transitory machine-accessible storage medium of claim 1, further providing instructions that, when executed by the machine, will cause the machine to perform further operations, comprising:
generating a visibility indicator that indicates a proportion of interior surface area of the tubular anatomical structure surrounding the lumen that was viewable versus unviewable in the live video feed as the endoscope traverses a longitudinal section of the tubular anatomical structure.

9. The at least one non-transitory machine-accessible storage medium of claim 8, wherein the proportion of interior surface area that was viewable versus unviewable is based upon a temporal integration window ranging between 5 to 30 seconds.

10. The at least one non-transitory machine-accessible storage medium of claim 8, wherein the visibility indicator discretizes the proportion of interior surface area into four or less ranges.

11. The at least one non-transitory machine-accessible storage medium of claim 8, wherein the visibility indicator discretizes the proportion into three discrete ranges that are color coded.

12. The at least one non-transitory machine-accessible storage medium of claim 1, wherein the endoscope comprises a colonoscope, the tubular anatomical structure comprises a colon, and the endoscopy procedure comprises a colonoscopy procedure.

13. The at least one non-transitory machine-accessible storage medium of claim 12, wherein generating the observation location map comprises generating the observation location map during a withdrawal phase of the colonoscopy procedure.

14. At least one non-transitory machine-accessible storage medium that provides instructions that, when executed by a machine, will cause the machine to output a signal for rendering a user-interface to a display, the user-interface adapted for navigating an endoscope through a lumen of a tubular anatomical structure during an endoscopy procedure, the user-interface comprising:
a video region in which a live video feed received from the endoscope is displayed; and
an observation location map that depicts a point of observation from which the live video feed is acquired within the lumen relative to a cross-sectional depiction of the lumen as the endoscope longitudinally traverses the tubular anatomical structure within the lumen during the endoscopy procedure, wherein the observation location map comprises an observation point marker disposed within a cross-sectional perimeter shape depiction of the lumen and conveys a position of the point of observation relative to the cross-sectional perimeter shape depiction.

15. The at least one non-transitory machine-accessible storage medium of claim 14, further providing instructions that, when executed by the machine, will cause the machine to perform further operations, comprising:
generating a velocity indicator for display within the endoscopy user-interface, wherein the velocity indicator visually depicts in real-time a direction of longitudinal motion of the endoscope moving through the lumen and a magnitude of longitudinal motion of the endoscope moving through the lumen.

16. The at least one non-transitory machine-accessible storage medium of claim 15, wherein the velocity indicator comprises a dynamic bar graph that extends in a positive direction from a zero point to indicate a positive longitudinal motion of the endoscope moving through the lumen or extends in a negative direction from the zero point to indicate a negative longitudinal motion of the endoscope moving through the lumen.

17. The at least one non-transitory machine-accessible storage medium of claim 14, wherein the user-interface further comprises:
a visibility indicator that indicates a proportion of interior surface area of the tubular anatomic structure surrounding the lumen that was viewable versus unviewable in the live video feed as the endoscope traverses a longitudinal section of the tubular anatomical structure.

18. The at least one non-transitory machine-accessible storage medium of claim 17, wherein the proportion of interior surface area that was viewable versus unviewable is based upon a temporal integration window.

19. The at least one non-transitory machine-accessible storage medium of claim 18, wherein the visibility indicator discretizes the proportion of interior surface area into three discrete ranges that are color coded.

20. At least one non-transitory machine-accessible storage medium that provides instructions that, when executed by a machine, will cause the machine to perform operations comprising:
generating an endoscopy user-interface for display on a screen during an endoscopy procedure;
outputting a live video feed of a lumen of a tubular anatomical structure received from an endoscope during the endoscopy procedure for display within a video region of the endoscopy user-interface; and
generating a velocity indicator for display within the endoscopy user-interface, wherein the velocity indicator visually depicts in real-time a direction of longitudinal motion of the endoscope moving through the lumen and a magnitude of longitudinal motion of the endoscope moving through the lumen, wherein the velocity indicator is contemporaneously presented proximate to the live video feed within the endoscopy user-interface to provide real-time navigation context with the live video feed.

21. The at least one non-transitory machine-accessible storage medium of claim 20, further providing instructions that, when executed by the machine, will cause the machine to perform further operations, comprising:
generating an observation location map for display within the endoscopy user-interface, wherein the observation location map depicts a point of observation from which the live video feed is acquired within the lumen relative to a cross-sectional depiction of the lumen as the endoscope moves longitudinally along the tubular anatomical structure within the lumen during the endoscopy procedure.

22. At least one non-transitory machine-accessible storage medium that provides instructions that, when executed by a machine, will cause the machine to perform operations comprising:
generating an endoscopy user-interface for display on a screen during an endoscopy procedure;
outputting a live video feed of a lumen of a tubular anatomical structure received from an endoscope during the endoscopy procedure for display within a video region of the endoscopy user-interface; and
generating a visibility indicator that indicates a proportion of interior surface area of the tubular anatomical structure surrounding the lumen that was viewable versus unviewable in the live video feed as the endoscope traverses a longitudinal section of the tubular anatomical structure, wherein the visibility indicator discretizes the proportion of interior surface area into four or less ranges.

23. The at least one non-transitory machine-accessible storage medium of claim 22, further providing instructions that, when executed by the machine, will cause the machine to perform further operations, comprising:
generating an observation location map for display within the endoscopy user-interface, wherein the observation location map depicts a point of observation from which the live video feed is acquired within the lumen relative to a cross-sectional depiction of the lumen as the endoscope moves longitudinally along the tubular anatomical structure within the lumen during the endoscopy procedure.

24. The at least one non-transitory machine-accessible storage medium of claim 22, wherein the visibility indicator discretizes the proportion of interior surface area into three discrete ranges that are color coded.

* * * * *